(12) United States Patent
Nielsen

(10) Patent No.: US 12,370,074 B2
(45) Date of Patent: Jul. 29, 2025

(54) OSTOMY PRODUCT WITH ANTI-REFLUX DEVICE

(71) Applicant: Hollister Incorporated, Libertyville, IL (US)

(72) Inventor: Kenneth Nielsen, Fredensborg (DK)

(73) Assignee: HOLLISTER INCORPORATED, Libertyville, IL (US)

(*) Notice: Subject to any disclaimer, the term of this patent is extended or adjusted under 35 U.S.C. 154(b) by 333 days.

(21) Appl. No.: 18/028,600

(22) PCT Filed: Nov. 18, 2021

(86) PCT No.: PCT/US2021/059833
§ 371 (c)(1),
(2) Date: Mar. 27, 2023

(87) PCT Pub. No.: WO2022/115304
PCT Pub. Date: Jun. 2, 2022

(65) Prior Publication Data
US 2023/0363937 A1 Nov. 16, 2023

Related U.S. Application Data

(60) Provisional application No. 63/118,095, filed on Nov. 25, 2020.

(51) Int. Cl.
*A61F 5/445* (2006.01)
*A61F 5/44* (2006.01)

(52) U.S. Cl.
CPC ............ *A61F 5/445* (2013.01); *A61F 5/4405* (2013.01)

(58) Field of Classification Search
CPC ........................................ A61F 5/44
See application file for complete search history.

(56) References Cited

U.S. PATENT DOCUMENTS

4,084,590 A * 4/1978 Caraway ................. A61F 5/445
604/350
4,592,750 A 6/1986 Kay
(Continued)

FOREIGN PATENT DOCUMENTS

CN 208339652 U * 1/2019
CN 113081453 A * 7/2021 ........... A61F 5/4404
(Continued)

OTHER PUBLICATIONS

International Search Report issued by ISA/EPO in connection with PCT/US2021/059833 dated Mar. 10, 2022.
(Continued)

*Primary Examiner* — Philip R Wiest
*Assistant Examiner* — Matthew Wrubleski
(74) *Attorney, Agent, or Firm* — Klintworth & Rozenblat LLP

(57) ABSTRACT

A pouch for collecting biological fluids includes a body side wall and a distal side wall defining a collection chamber therebetween. An inlet opening is provided in the body side wall and an insert is mounted to the body side wall. The insert has an insert opening overlying the inlet opening. An anti-reflux device is disposed in the collection chamber. A first end of the anti-reflux device is mounted to the insert, overlying the insert opening. A second end of the device is mounted to the distal side wall. The anti-reflux device has a plurality of openings therein to provide flow communication from an interior of the anti-reflux device to the collection chamber.

20 Claims, 2 Drawing Sheets

(56) References Cited

U.S. PATENT DOCUMENTS

| | | | |
|---|---|---|---|
| 4,676,786 A | 6/1987 | Nishino | |
| 5,125,897 A | 6/1992 | Quinn et al. | |
| 5,364,378 A | 11/1994 | Denard | |
| 6,033,390 A | 3/2000 | von Dyck | |
| 6,352,526 B1 | 3/2002 | Cawood | |
| 8,388,586 B2 | 3/2013 | Weig | |
| 9,962,282 B2 * | 5/2018 | Chang | A61F 5/445 |
| 10,045,877 B2 | 8/2018 | Weig | |
| 10,478,329 B2 * | 11/2019 | Oberholtzer | A61F 5/445 |
| 10,478,330 B2 * | 11/2019 | Wiltshire | A61F 5/445 |
| 2006/0079854 A1 | 4/2006 | Kay et al. | |
| 2009/0163883 A1 | 6/2009 | Christensen et al. | |
| 2014/0163497 A1 * | 6/2014 | Hannan | A61F 5/443 |
| | | | 156/60 |

FOREIGN PATENT DOCUMENTS

| | | |
|---|---|---|
| JP | 2013-545544 A | 12/2013 |
| WO | 2019242828 A1 | 12/2019 |

OTHER PUBLICATIONS

Written Opinion issued by ISA/EPO in connection with PCT/US2021/059833 dated Mar. 10, 2022.
International Preliminary Report on Patentability issued by WIPO in connection with PCT/US2021/059833 dated Jun. 8, 2023.

\* cited by examiner

OSTOMY PRODUCT WITH ANTI-REFLUX DEVICE

BACKGROUND

The present disclosure pertains to an ostomy product, such as an ostomy pouch for collecting biological excretions (such as excretions from a surgically-created stoma). More particularly, the present disclosure pertains to an anti-reflux device in the ostomy product to direct the excretions away from, and minimize the return of excretions to the inlet of the product.

Ostomy appliance users have identified issues with skin irritation and adhesive swelling when the user is lying down for an extended period of time. It has been observed that these issues arise because excretions, such as liquid output, can accumulate in the convex area around the stoma and may not be directed away from the pouch inlet and the stoma. These issues can arise with both ostomy and urostomy patients and are particularly problematic with ostomy and urostomy patients using pouches with convex skin barriers.

Accordingly, there is a need for a device in an ostomy product that allows excretions to be directed away from the ostomy product inlet and the stoma area. Desirably, such as device facilitates transporting excretions, such as liquid output, away from the ostomy product inlet and the stoma area to enhance conditions for the stoma and skin surface.

SUMMARY

An ostomy device such as an ostomy pouch for collecting biological fluids includes an anti-reflux device to direct excretions away from the ostomy device inlet and the stoma area. The anti-reflux device facilitates transporting excretions, such as liquid output, away from the device inlet and the stoma area to enhance conditions for the stoma and skin surface.

In an aspect, the pouch includes a body side wall and a distal side wall defining a collection chamber therebetween. An inlet opening is provided in the body side wall, and an insert is mounted to the body side wall. The insert has an insert opening overlying the inlet opening.

The anti-reflux device is disposed in the collection chamber. In embodiments, the anti-reflux device is a tube, such as a film tube. A first end of the anti-reflux tube is mounted to the insert and overlies the insert opening. A second end of the anti-reflux tube is mounted to the distal side wall. In embodiments, the anti-reflux tube is mounted to the insert to form a peripheral seal of the tube at the insert and is mounted to the distal side wall to form a peripheral seal of the tube at the distal side wall. The anti-reflux tube has a plurality of openings therein to provide flow communication from an interior of the anti-reflux device to the collection chamber.

In embodiments, the tube has a circular cross-section. The plurality of openings in the tube wall can be formed as arcuate slits, cruciform slits, perforations, such as micro-perforations and the like.

In an aspect, a pouch for collecting biological fluids includes a body side wall and a distal side wall defining a collection chamber therebetween, an inlet opening in the body side wall, and an insert mounted to the body side wall. The insert has an insert opening overlying the inlet opening.

An anti-reflux tube extends between the insert and the distal side wall. The tube overlies the insert opening. The tube has a plurality of openings in a wall thereof to provide flow communication from an interior of the anti-reflux tube to the collection chamber. The openings in the wall of the anti-reflux tube provide the only flow path from the inlet to the collection chamber.

In an embodiment, a first end of the anti-reflux tube is sealed to the insert and a second end of the anti-reflux tube is sealed to the distal side wall. The plurality of openings in the anti-reflux tube wall can be arcuate slits, cruciform or cross-cut slits, perforations, such as micro-perforations and the like.

Other aspects and advantages will become more apparent from the following detailed description when taken in conjunction with the accompanying drawings.

DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
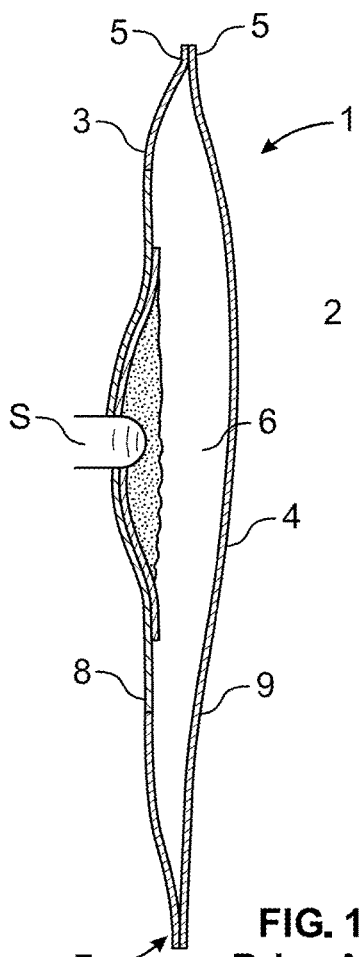
FIG. 1 is a sectional illustration of a prior art ostomy pouch.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Referring now to the figures and briefly first to FIG. 1, there is shown a known ostomy pouch 1. The pouch 1 has a body 2 formed by, for example, sealing two films 3, 4 to one another about their respective peripheries 5 to define a collection chamber 6.

The films 3, 4 may be sealed to one another by methods such a heat sealing and the like. A valve (not shown), if used, may be similarly sealed to the pouch 1 at a bottom opening (indicated generally at 7). Suitable methods for sealing the pouch walls/films 3, 4 to one another and the valve to the pouch films 3, 4 will be recognized by those skilled in the art. The pouch 1 may be provided with non-woven layers (not shown) on each of the body and distal sides 8, 9 of the pouch 1, or only on one of the body or distal sides 8, 9 of the pouch 1.

Figure 2:
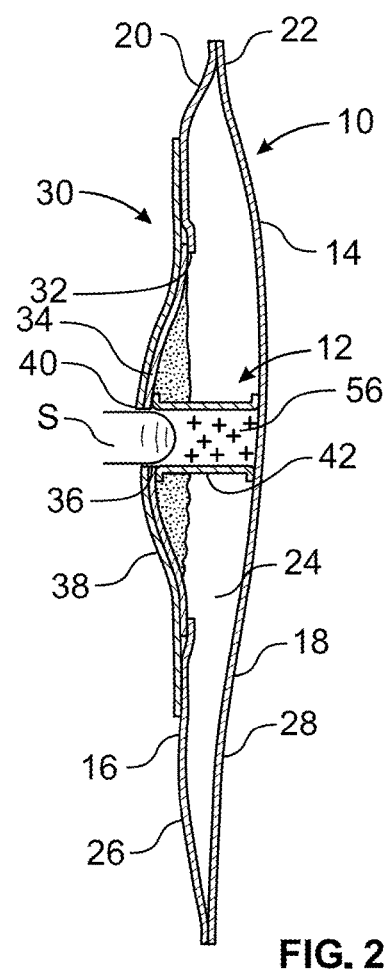
FIG. 2 is a sectional illustration of an ostomy pouch with an embodiment of an anti-reflux device in the ostomy pouch.
Figure 4:
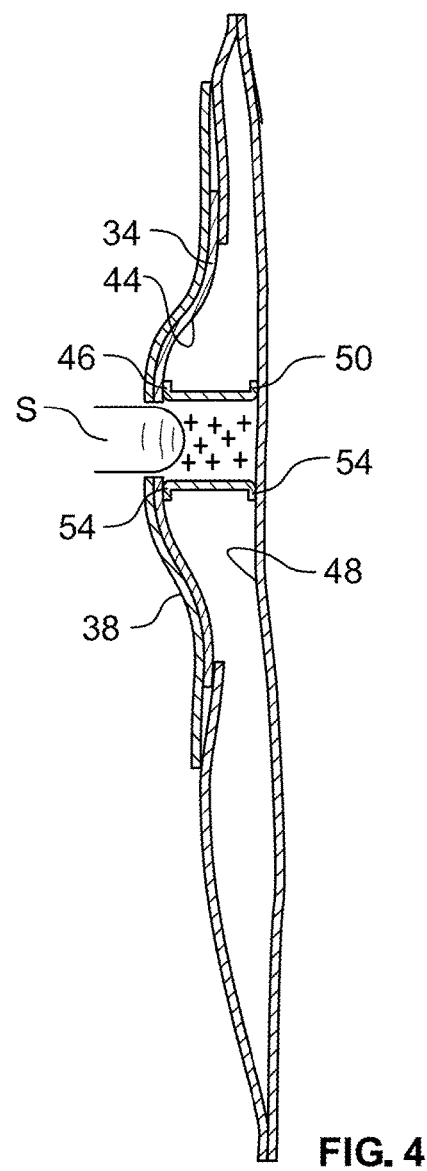
FIG. 4 is another sectional illustration of an ostomy pouch with the anti-reflux device.

Referring to FIGS. 2 and 4, there is shown a sectional illustration of an ostomy pouch 10 with an embodiment of an anti-reflux device 12. The pouch 10 includes has a body 14 formed by, for example, sealing two films 16, 18 to one another about their respective peripheries 20, 22 to define a collection chamber 24. The films 16, 18 can define a body side wall 26 and a distal side wall 28.

Although not shown, the pouch 10 can include, at about the bottom thereof, an opening that defines a valve, or into which a valve may be fitted and secured. The films 16, 18 may be sealed to one another by methods such a heat sealing and the like. The valve, if used, may be similarly sealed to the pouch 10 at the bottom opening. Suitable methods for sealing the pouch films 16, 18 to one another and the valve to the pouch films 16, 18 will be recognized by those skilled in the art. The pouch 10 may be provided with non-woven layers (not shown) on the outside of one or both of the body side wall 26 and distal side wall 28 of the pouch 10.

In a top section 30 of the pouch 10, an inlet opening 32 is provided in the body side wall 26, through which waste enters the pouch 10 from a stoma S. An insert 34 is mounted to an outside surface of the body side wall 26. In embodiments, the insert 34 is a convex insert (convex relative to the user), and in embodiments, the convex insert 34 is a soft convex insert. The insert 34 has an opening 36 that aligns with the pouch inlet opening 32. The insert opening 36 is about at the apex of the convexity.

A barrier 38 is poisoned on and outboard of the insert 34. The barrier 38 is the material that secures the ostomy pouch 10 to the user and provides a barrier to prevent stomal excretions from contact with the peristomal skin. The barrier 38 thus serves two functions—to secure the pouch 10 to the user and to prevent or minimize skin irritation due to excretion contact with the user's skin.

The barrier 38 is also convex and typically includes a skin barrier having an adhesive and an inlet opening 40 for receiving the stoma S. The convex insert 34 is arranged adjacent the skin barrier 38.

An embodiment of the anti-reflux device 12 is seen in FIGS. 2-4 and 5B. In an embodiment, the anti-reflux device 12 is formed as a tube 42 that extends between a rear wall 44 of the insert 34 and the distal side wall 28. The tube 42 can be a film, similar to the first or second wall films 16, 18, or a different film. The tube 42 is sealed to the insert 34 at the opening 36 and overlies the opening 36. In an embodiment, the tube 42 is sealed fully around its periphery 46 to the insert 34. Likewise, an opposite end of the tube 42 is sealed to an inside surface 48 of the distal side wall 28, and can be sealed fully around its periphery 50 to the distal side wall 28. In an embodiment, the tube 42 forms flanges 54 the at its ends to facilitate sealing the tube 42 to the insert 34 and the distal side wall 28. Although the device 12 is described as a tube 42, it will be understood that the tube 42 need not be a round tube. Rather, the tube 42 can have a wide variety of cross-sectional shapes, and can be formed from a sheet and sealed along a longitudinal side seal.

To provide a flow path P from the tube 42 into the pouch collection chamber 24 (out of the tube 42), the anti-reflux device 12 includes a plurality of through-wall openings 56. The openings 56 can take many forms, sizes and locations in the tube 42. The openings 56 in the tube 42 provide the only flow path P from the pouch inlet 32 into the collection chamber 24.

Figure 5A:
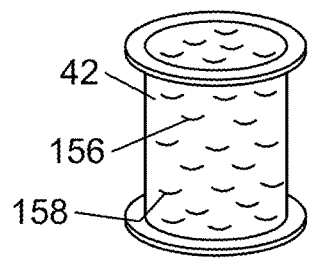
FIGS. 5A-5C are perspective illustrations of various embodiments of the anti-reflux device.

As seen in FIG. 5A, in an embodiment, the openings 56 are arcuate or curved openings 156, formed in a staggered arrangement longitudinally and circumferentially about the tube 42. The openings 156 can be in a random arrangement in the tube 42, or in other locations in, and arrangements, around the tube 42. The openings 156 can be formed such that the apex 158 of the curve is located in the downstream direction of flow of the excretion.

Figure 3:
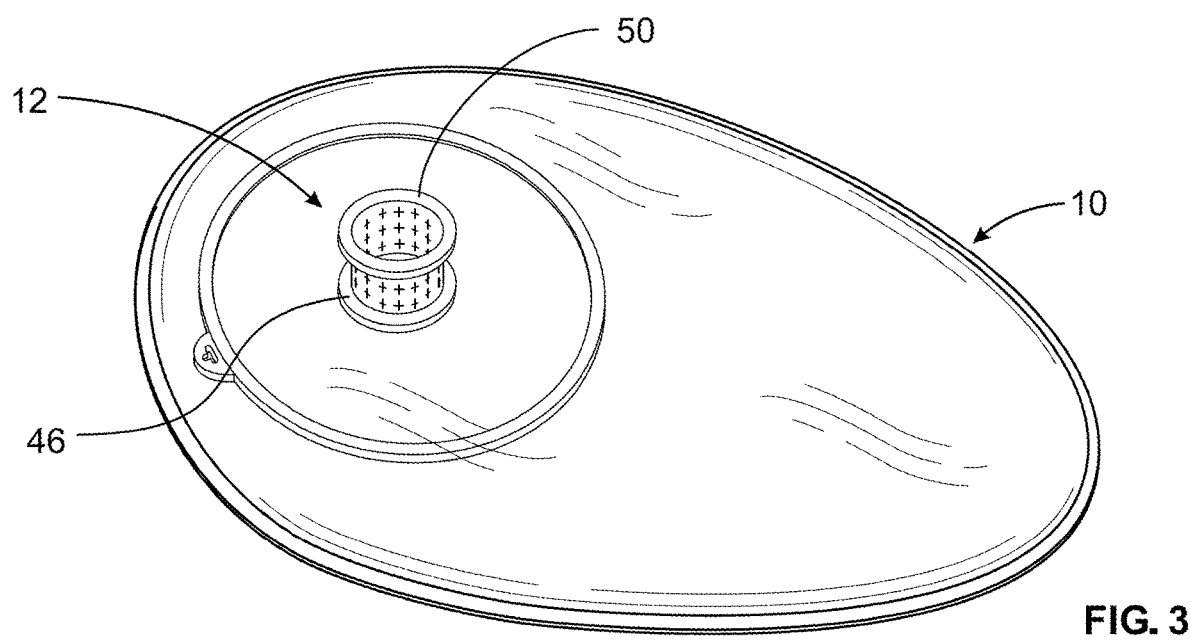
FIG. 3 is a perspective illustration of an ostomy pouch with an embodiment of the anti-reflux device in the ostomy pouch.
Figure 5B:
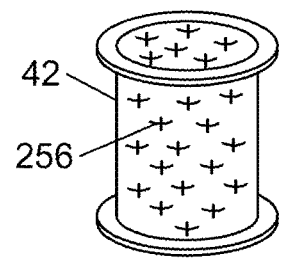
Figure 5C:
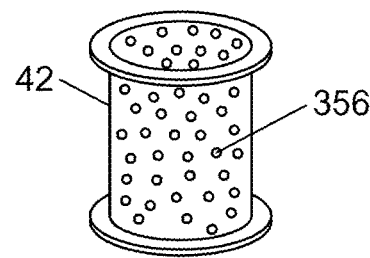

FIGS. 2, 3 and 5B illustrate an embodiment in which the openings 56 are formed as cruciform or cross-cut slits 256 in the tube wall 42. Again, the openings 256 can be formed in a staggered arrangement longitudinally and circumferentially about the tube 42, in a random arrangement in the tube 42, or in other locations in, and arrangements around, the tube 42. FIG. 5C illustrates yet another embodiment in which the openings 56 are formed as perforations 356, such as micro-perforations in the tube 42 wall. As with the openings 156 and 256 shown in FIGS. 5A and 5B, the openings 356 can be formed in a staggered arrangement longitudinally and circumferentially about the tube 42, in a random arrangement in the tube 42, or in other locations in, and arrangements around, the tube 42.

It will be appreciated that the present anti-reflux device 12 allows excretions to be directed away from the ostomy pouch inlet 32 and the stoma S area. The present anti-reflux device 12 facilitates transporting excretions, such as liquid output, away from the ostomy pouch inlet 32 and the stoma S area to enhance conditions for the stoma S and skin surface.

In an embodiment, an ostomy pouch appliance 10 may include an ostomy wafer attached to a body side wall 26 of the pouch and anti-reflux device 12 attached to an inner surface of of the wafer at one end and an inner surface of a distal wall 28. The wafer may include a convex insert 34 and a skin barrier layer 38, wherein the convex insert 34 may be mounted to the body side wall 26. The ostomy pouch appliance 10 may include an inlet opening 36 defined through the wafer and the pouch.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A pouch for collecting biological fluids comprising:
   a body side wall and a distal side wall defining a collection chamber therebetween;
   an inlet opening provided in the body side wall;
   an insert mounted to the body side wall, the insert having an insert opening overlying the inlet opening; and
   an anti-reflux device disposed in the collection chamber, a first end of the anti-reflux device mounted to the insert and overlying the insert opening, a second end of the anti-reflux device mounted to the distal side wall, the anti-reflux device having a plurality of openings therein to provide flow communication from an interior of the anti-reflux device to the collection chamber.

2. The pouch of claim 1, wherein the anti-reflux device is a tube.

3. The pouch of claim 2, wherein the tube is formed from a film.

4. The pouch of claim 2, wherein the tube has a circular cross-section.

5. The pouch of claim 2, wherein the tube is mounted to the insert to form a peripheral seal of the tube at the insert.

6. The pouch of claim 2, wherein the tube is mounted to the distal side wall to form a peripheral seal of the tube at the distal side wall.

7. The pouch of claim 1, wherein the plurality of openings are formed in the device as arcuate slits in a wall of the device.

8. The pouch of claim 1, wherein the plurality of openings are formed in the device as cruciform slits in a wall of the device.

9. The pouch of claim 1, wherein the plurality of openings are formed in the device as perforations in a wall of the device.

10. The pouch of claim 9, wherein the perforations are micro-perforations.

11. A pouch for collecting biological fluids comprising:
a body side wall and a distal side wall defining a collection chamber therebetween;
an inlet opening provided in the body side wall;
an insert mounted to the body side wall, the insert having an insert opening overlying the inlet opening; and
an anti-reflux tube having a first end mounted to the insert and overlying the inlet opening and the insert opening, a second end mounted to the distal side wall, tube first and second ends sealed to insert and distal side wall, respectively, the anti-reflux tube having a plurality of openings in a wall of the tube to provide flow communication from an interior of the anti-reflux tube to the collection chamber.

12. The pouch of claim 11, wherein the plurality of openings are formed in the device as arcuate slits in a wall of the device.

13. The pouch of claim 11, wherein the plurality of openings are formed in the device as cruciform slits in a wall of the device.

14. The pouch of claim 11, wherein the plurality of openings are formed in the device as perforations in a wall of the device.

15. A pouch for collecting biological fluids comprising:
a body side wall and a distal side wall defining a collection chamber therebetween;
an inlet opening provided in the body side wall;
an insert mounted to the body side wall, the insert having an insert opening overlying the inlet opening; and
an anti-reflux tube extending between the insert and the distal side wall, the anti-reflux tube overlying the inlet opening and the insert opening, the anti-reflux tube having a plurality of openings in a wall of the anti-reflux tube to provide flow communication from an interior of the anti-reflux tube to the collection chamber, the openings in the wall of the anti-reflux tube providing the only flow path from the inlet to the collection chamber.

16. The pouch of claim 15, wherein a first end of the anti-reflux tube is sealed to the insert and a second end of the anti-reflux tube is sealed to the distal side wall.

17. The pouch of claim 15, wherein the plurality of openings are formed in the anti-reflux tube as arcuate slits in the wall of the anti-reflux tube.

18. The pouch of claim 15, wherein the plurality of openings are formed in the anti-reflux tube as cruciform slits in the wall of the anti-reflux tube.

19. The pouch of claim 15, wherein the plurality of openings are formed in the anti-reflux tube as perforations in the wall of the anti-reflux tube.

20. The pouch of claim 15, wherein the anti-reflux tube is formed from a film.

\* \* \* \* \*